United States Patent [19]

Katchis et al.

[11] Patent Number: 4,622,979
[45] Date of Patent: Nov. 18, 1986

[54] USER-WORN APPARATUS FOR MONITORING AND RECORDING ELECTROCARDIOGRAPHIC DATA AND METHOD OF OPERATION

[75] Inventors: Louis J. Katchis, Miami; Michael P. Bumgarner, N. Palm Beach, both of Fla.

[73] Assignee: Cardiac Monitoring, Inc., North Palm Beach, Fla.

[21] Appl. No.: 585,790

[22] Filed: Mar. 2, 1984

[51] Int. Cl.⁴ .................................................. A61B 5/04
[52] U.S. Cl. ..................................... 128/702; 128/904
[58] Field of Search .............. 128/695, 696, 697, 702, 128/703, 704, 709, 710, 711, 712, 904

[56] References Cited

U.S. PATENT DOCUMENTS

| 3,426,150 | 2/1969 | Tygart | 128/904 |
|---|---|---|---|
| 3,569,852 | 3/1971 | Berkovits | 128/696 |
| 3,587,564 | 6/1971 | Hagan et al. | 128/711 |
| 3,799,148 | 3/1974 | Rowen | 128/711 |
| 3,824,990 | 7/1974 | Baule | 128/702 |
| 3,871,363 | 3/1975 | Day | 128/697 |
| 3,934,267 | 1/1976 | Kosaka et al. | 128/711 |
| 4,006,737 | 2/1977 | Cherry | 128/710 |
| 4,417,306 | 11/1983 | Citron et al. | 128/710 |

*Primary Examiner*—William E. Kamm
*Attorney, Agent, or Firm*—Duckworth, Allen, Dyer & Pettis

[57] ABSTRACT

Apparatus is disclosed that can be worn by a user for monitoring and recording electrocardiographic data from the user. The apparatus provides for continuous storage of predetermined time increments of such data in digital form, with new data being stored over preexisting data and the apparatus being operable by the user halt further such recordings to hold for subsequent output the data corresponding to such a predetermined time increments.

24 Claims, 7 Drawing Figures

USER-WORN APPARATUS FOR MONITORING AND RECORDING ELECTROCARDIOGRAPHIC DATA AND METHOD OF OPERATION

FIELD OF THE INVENTION

This invention relates generally to the field of apparatus for monitoring and recording electrocardiographic data. More particularly, it relates to such apparatus that is compact and may be carried or worn by a user. The invention further relates to such apparatus and related method that can record such electrocardiographic data for later playback and analysis.

BACKGROUND OF THE INVENTION

Electrocardiographic monitoring and recording apparatus for use in hospital environments has long been known. However, such apparatus is generally bulky and requires that the person being monitored be confined to a bed or chair or an area of very limited mobility.

More recently, compact apparatus has been developed that may be worn or carried by a user for monitoring electrocardiographic data and transmitting that data directly to a telephone handset to recording and analyzing equipment at a centralized location. Such apparatus is exemplified by the Cardiotel ECG transmitter manufactured by Instromedix. Even more recently there has been developed such compact apparatus that both records an electrocardiogram upon command of a user and then, at a convenient subsequent time, plays back and transmits that data through a telephone handset to apparatus at a remote location for analysis of the data. This recording and transmitting apparatus is exemplified by the CardioDiary apparatus manufactured by Instromedix, the TAM II apparatus from Cardiac Data Corp., Cardiobeeper from Survival Tech and the SAMM apparatus from Dart Medical.

While all of these prior devices provide certain benefits, they have suffered from several shortcomings and deficiencies. With their limited recording capabilities, they all depend upon user manipulation at the onset of a symptomatic episode to actuate the apparatus and initiate their recording. This precludes the recording and analysis of electrocardiographic data leading up to the synptomatic episode, which could provide important data surrounding the onset of the episode. Thus, the attending physician may be unable to obtain important data.

SUMMARY OF THE INVENTION

It is an object of the present invention to provide such user-worn cardiac monitoring and recording apparatus that overcomes the deficiencies of the prior art. More particularly, it is an object of this invention to provide such apparatus with a continuous storage capability so that, upon occurrence of a symptomatic episode, data can be recovered to provide electrocardiographing data leading up to that episode.

To achieve the foregoing, as well as other objects, this invention provides for user-worn apparatus and related method for monitoring and recording electrocardiographic data from a user, in which the apparatus includes at least one sensing electrode for engaging the body of the user, signal amplifying structure connected to the electrode for receiving and amplifying the analog electrical signals from the electrode, devices for converting those analog signals to digital signals, selectively operable continuous signal storage structure for receiving and storing the digital signals in predetermined time increments, apparatus operatively connected to the signal storage structure for halting further storage of the digital signals upon the occurrence of a predetermined event and structure for providing output of the storage signals for subsequent analysis of the data. The continuous signal storage structure provides for each succeeding time increment of signals to be stored over signals of the immediately preceeding time increment, so that the signals stored therein at any given time comprise the signals received and stored during the immediately preceeding time increment.

DESCRIPTION OF PREFERRED EMBODIMENT OF THE APPARATUS

A preferred embodiment of the apparatus of this invention will be described in detail in connection with the drawings in which.

DESCRIPTION OF A PREFERRED EMBODIMENT

Figure 1:
FIG. 1 is a representation of a user wearing the preferred embodiment of the apparatus of this invention.

A preferred embodiment of the apparatus of Fig. 1 is illustrated in the drawings. FIG. 1 illustrates the apparatus as worn by a user. In this illustration the sensing electrode 2 is conveniently illustrated as an arm band type electrode, although numerous other types of electrodes for engaging a finger, or sticking onto a chest or other parts of the body, or other types, may be used with equally satisfactory results. This electrode is connected through wire and plug 4 to the main monitoring and recording unit generally indicated by reference numeral 6. This unit 6 is illustrated more clearly in FIGS. 2 through 5.

Figure 2:
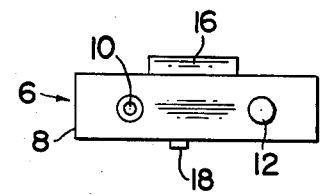
FIG. 2 is a top plan view of a preferred embodiment of the apparatus of this invention.
Figure 3:
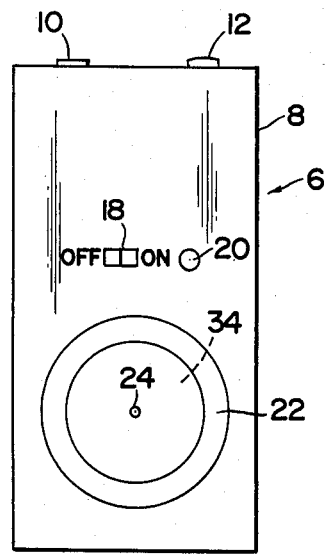
FIG. 3 is a front elevational view of the apparatus of FIG. 2.
Figure 4:
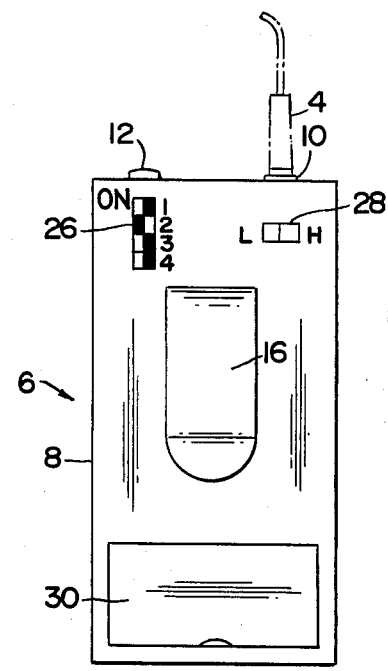
FIG. 4 is a rear elevation of the apparatus of FIGS. 2 and 3.

FIGS. 2 through 4 illustrate the external features of the principal unit of this apparatus. These features include the case 8, which may suitably be molded of a rigid plastic material, jack 10 into which is received plug 4 connecting the electrode 2 to the unit. User activation switch 12 may be a momentary push button switch to initiate the recording feature of this apparatus that will be discussed more fully below. On the back of the case 8 may suitably be provided a belt clip 16.

In the front view of FIG. 3 is illustrated the main power switch 18, which may be a slide switch, and indicator 20, which may suitably be a light emitting diode, to indicate by flashing when the battery for the unit is low. Also on the front may be provided a recessed ring 22 for receiving a telephone mouthpiece for transtelephonic transmission of the data in this apparatus. This data may suitably be provided by a speaker 34 (not shown) as an audio signal, to be described below, transmitted through the aperture 24 that may be concentric with the recessed ring 22.

In the rear view of FIG. 4 of the apparatus is illustrated both the timing mode switch 26 and the bandwidth switch 28. As shown, the timing mode switch in this preferred embodiment may have four positions. This switch 26 may be slightly recessed and adjustable among the four positions by use of a small screwdriver or similar device, such that a doctor providing the monitoring apparatus may set or program the timing mode with little chance for inadvertent changing of that setting by the user. Similarly, the frequency response switch 28 may also be recessed to guard against accidental changing of its position. This switch 28 may be selectively operable between position "L" for full frequency response including low frequency signals, and position "H" permitting passage of input signals whose frequencies are above a predetermined threshold. At the lower portion of the back of the device may be provided the battery door 30 enclosing the battery compartment that may suitably house a nine volt battery.

Figure 5:
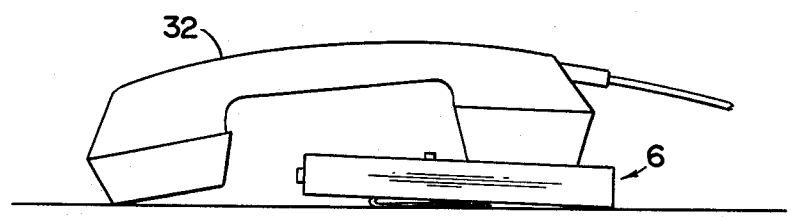
FIG. 5 is a side elevational view of the apparatus of FIGS. 2 through 4 illustrating its use in connection with a telephone handset.

In the side elevation of FIG. 5 the unit 6 is illustrated as engaging a telephone handset 32, such as might be used in the signal transmitting function of the apparatus 6. In this illustration the transmitter or mouthpiece portion of the telephone handset is placed to engage the recessed ring 22 so that audio signals from the speaker 34 will be directed through aperture 24 into the telephone transmitter.

Figure 6:
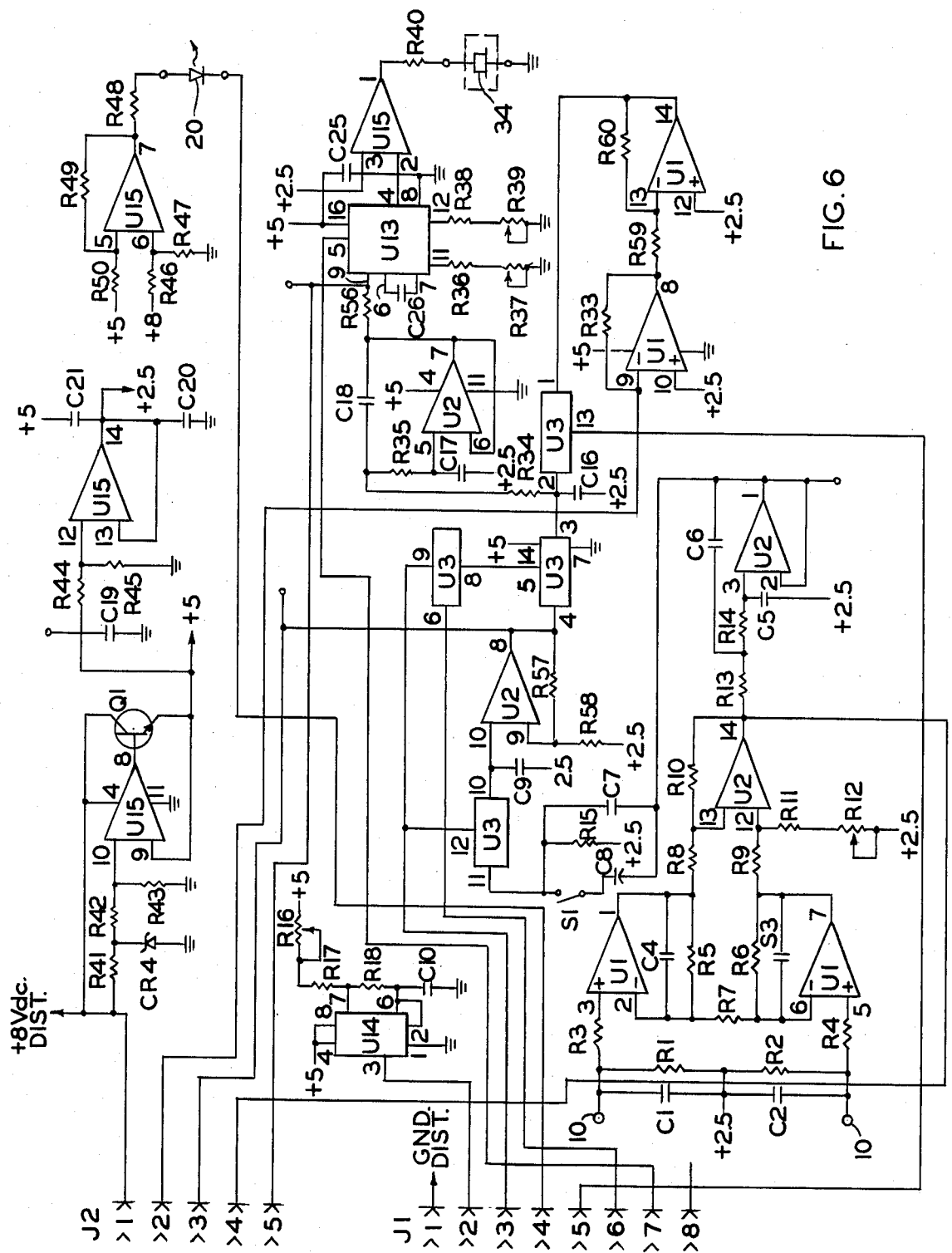
FIG. 6 is a schematic diagram of the analog signal board contained within the apparatus of FIGS. 2 through 5.
Figure 7:
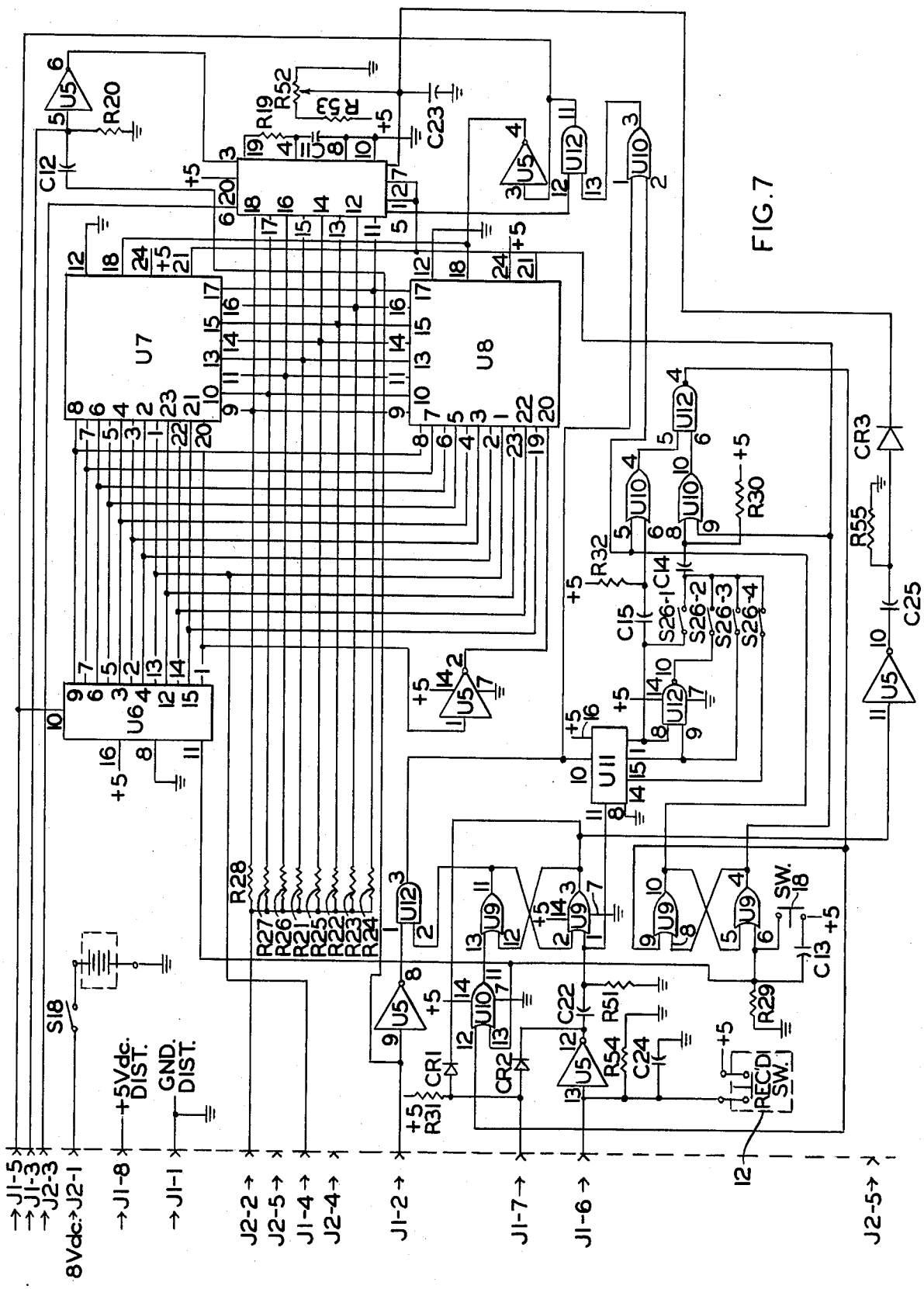
FIG. 7 is a schematic diagram of the digital circuit board of the apparatus of FIGS. 2 through 5.

The circuitry of a preferred embodiment of this apparatus is illustrated in the diagrams of FIGS. 6 and 7. FIG. 6 illustrates the circuitry associated primarily with the analog signal processing portion of the apparatus, and FIG. 7 illustrates that circuitry primarily associated with the digital signal handling portion thereof.

At the extreme left hand side of FIG. 6 are schematically illustrated the pins of two connectors J1 and J2. Suitably, connector J1 may have eight pins and connector J2 may have 5. For convenience of notation the various pins of J1 will be referred to as J1-1, J1-2 ... J1-8, and the pins of connector J2 will be referred to as J2-1, J2-2 ... J2-5.

In the circuit diagram of FIG. 6 the input signal from the patient electrode is introduced through the two leads coming from the jack 10 shown in FIGS. 2 through 4. The signal from this electrode is introduced into an amplifier configured as an instrumentation amplifier based on an operational amplifier, such as a Texas Instruments TL064CN. This operational amplifier, designated U1, is an individual unit possessing 14 input and output pins. However, for simplicity of illustration, this operational amplifier, designated U1 is functionally illustrated in FIG. 6 in four separate blocks to illustrate more clearly the connection of the 14 pins, with each such pin numbered. The input circuit includes resistors R1, R2, R3 and R4 and capacitors C1 and C2. Resistors R1 and R2 act as high impedance returns for the direct and alternating currents to the common mode point therebetween, which is the plus 2.5 volt supply. This establishes the necessary biasing for the rest of the amplifier. C1 and C2 are bypass capacitors for high frequencies that might come in through the patient electrode cable and through jack 10. The differential and common mode signals are applied to the input amplifier through current limiting resistors R3 and R4 to limit any potentially damaging currents that could result from a transient entering the transmitter from the patient electrode cable.

Feedback resistors R5 and R6 and common mode gain resistor R7 set the overall gain of the input stage of the amplifier. Capacitors C3 and C4 serve to reduce the gain of the amplifier at any undesired high frequencies. From this circuitry the amplified differential signal is applied to a single ended amplifier stage made up of resistors R8, R9, R10, R11 and R12 and the pin 14 output of operational amplifier U2. This operational amplifier, which may suitably be the same type of component as U1, is likewise illustrated for clarity as several separate modules despite its single unitary configuration. This amplifying stage serves to strip the common signal from the desired differential signal and may suitably provide a differential gain of 52 while allowing only a common mode gain of 1. Resistor R12 serves to tune the optimum common mode rejection by balancing out the various components.

A low pass filter stage is comprised of resistors R13 and R14, capacitors C5 and C6 and the output pin 1 of operational amplifier U2. This low pass filter stage is designed to remove frequency components greater than 50 Hz and utilizes components chosen to follow a second order, low-pass Tchebychev VCVS filter design with a cutoff frequency of about 45 Hz.

At this point the signal has been amplified and filtered but still contains the dc component from the electrode connection of the patient. Accordingly, a switch selectable high pass filter is provided to remove the very low frequency and dc component of the patient signal. This selectable high pass filter is comprised of capacitor C7 and C8, resistor R15 and switch S1. When switch S1 is open, the capacitor C7 and resistor R15 allow frequencies above 1 Hz to pass. When switch S1 is closed, capacitor C8, in parallel with C7, and resistor R15 allow frequencies above 0.05 Hz to pass. These frequencies are the 3dB down cutoff frequencies of the high pass filter. The resultant ac component signal is biased to the common mode signal ground 2.5 volt supply. This signal is applied to the input of integrated circuit electronic switch U3 pin 11.

This electronic switch U3 is preferably a C-MOS multiplexer such as Motorola type MC14066BCP. This switch U3 is controlled by a clock signal from the digital board (described below) at pin 12. The clock signal briefly switches on the electronic switch U3 at a rate of a master clock signal, suitably 100 Hz. A resultant sample of the signal is switched through output pin 10 of U3 and to capacitor C9. Capacitor C9 serves as a sample and hold capacitor for the periods between samples. Thus, this circuitry may serve as means for periodically sampling the analog signal received from the amplifier and for retaining that signal sample until a subsequent periodic signal sample is received. In this way, the signal applied to the analog to digital converter (to be described below) is steady during the time it is being converted. Thus also the analog signals converted by the analog to digital converter comprise the sequential signal samples so retained by the sample and hold capacitor C9. The held signal is applied to the input of buffer amplifier U2 at pin 9. This amplifier is configured to have a high input impedance and have a noninverting gain of approximately 21, set by resistors R57 and R58.

The main clock of the transmitter, located on the analog board schematically depicted in Fig. 6, is designed around the integrated circuit timer U14, which may conveniently be an Intersil type ICM7555PA. This is a C-MOS version of the type 555 timer incorporated to reduce battery drain. The oscillator timing for the circuit is set by the resistor string R16, R17 and R18, as well as the capacitor C10. Resistor R16 sets the calibration of the circuit, which preferably is set to 100 Hz during calibration testing. The values of the timer circuit suitably set the output pulse to approximately eight microseconds. This brief period serves to reduce battery consumption by the random access memory devices when they are utilized for reading or storing.

With reference now to the digital circuit board schematically represented in FIG. 7, the analog to digital converter (ADC) U4 is preferably a single integrated circuit, such as a National Semiconductor ADC0804LCN, operating on the five volt supply and utilizing a successive approximation method of analog to digital conversion. The internal clock of the ADC of this preferred embodiment operates at about 640 KHz and is set by the resistor R19 and capacitor C11. The network formed by resistor R52 and R53 and capacitor C23 serves as an offset adjustment to set the zero voltage level of the ADC U4. Analog signals to be converted arrive at pin 6 of the converter U4 from the analog board over the interconnect J2-3. These signals are converted to an eight binary bit code on command of the convert signal at pin 3 of the ADC U4.

The converted signal is derived from the main clock U4, described above. This main clock signal, which appears as a negative going pulse for eight microseconds, is differentiated by the network of capacitor C12 and resistor R20. The positive going edge of the clock generates a pulse that is sent over the interconnect J1-3 to the sample and hold circuit of the input amplifier (described above), thus holding a new analog sample. This positive pulse is also logically inverted by integrated circuit U5, which may suitably be a Motorola MC14069BCP. As with other integrated circuits, this single device U5 is schematically represented in FIG. 7 as a plurality of devices for purposes of clarity in the circuit diagram. After being inverted at pin 6 of the device U6, the pulse appears as a negative going pulse. The positive going edge of this pulse triggers the ADC to effect the desired conversion. Thus, by delaying the convert signal in this way, the analog signal applied to the input is new and stable at the time the ADC effects its conversion.

When the ADC, device U4, completes a conversion, a negative going pulse appears at pin 5 thereof. This pulse passes through the negative logic OR gate of device U12 at pin 11. This pulse appears at the clock input of the 12 binary bit counter integrated circuit U6, which may suitably be a Motorola MC14040BCP. Thus, at the end of a conversion the address counter U6 is updated to the next succeeding address. This pulse also crosses to the analog board over the interconnect J1-5 to the sample and hold circuit of the output stage, which will be described below. Thus, the value of the output circuit is updated. This pulse is also logically inverted by integrated circuit U5 at pin 4, whose output is applied to the "chip enable" input of the two random access memory (RAM) integrated circuits U7 and U8. These RAM devices are preferably of the C-MOS type and may suitably be Toshiba TC5516AP units. Thus, when the conversion is complete, the address counter has been updated, the sample and hold circuit has been updated, and the RAM memories are momentarily enabled to store the next digital value arriving from the ADC.

The random access memory (RAM) system comprises a selectively operable continuous signal storage means and includes RAM devices U7 and U8 and the address counter U6. While the transmitter is in the continuous storing mode, as opposed to the record mode and output producing or playback mode, the address counter U6 is counting up as each of the update pulses come in from the ADC. When the counter reaches its full count, it goes on through to zero, thus beginning again. The counter U6 is a 12 bit binary counter enabling a full address count of 4096 locations. The RAM memory devices U7 and U8 each contain 2,048 locations, which may store eight bits each, for a total of 4,096 such locations. The most significant bit of the address counter U6, from pin 1 thereof, selects which of the two RAM devices U7 or U8 are to be enabled, through chip enable pin 20 of the respective devices U7 and U8. RAM device U7 is enabled when counter U6 pin 1 is at logic zero. and RAM device U8 is enabled when counter U1 pin 1 is at logic 1. This is an accomplished by virtue of the logic inverter U5 pin 2.

The eight databit leads (pins 9 through 11 and 13 through 17) of the RAM devices U7 and U8 and of the ADC (pins 11 through 18 of device U4) are wired together to form a data bus. These connections also are in common with the digital to analog converter (DAC) formed by resistors R21 through R28. This eight bit binary data is available on the data bus whenever the apparatus is in the storing mode, record mode and the playback mode, but not in the standby mode. The explanation of the different modes and their controls is as set forth below.

The apparatus operates in any of four modes when powered on by the on/off switch S18, which corresponds to the switch 18 shown in FIG. 3. In the first mode, the unit is in the continuous storage mode, commencing immediately after the activation of the power switch to an "on" position. In this continuous storage mode the digital signals are continuously stored in the RAM devices U7 and U8 in the predetermined time increments, which, in this embodiment are forty seconds each. This means that, as each forty seconds of data has been stored, the next incoming data is stored over the oldest preceding data. Thus, at any given instant there is stored in the memory the preceding forty seconds of data.

When the power switch is turned on, an automatic reset function is generated by the charging of capacitor C13 through resistor R29. The brief positive pulse resets timer U6 directly and resets the mode control flipflop made up of device U9 pins 10 and 4. This device U9 may suitably be a dual input NOR gate, such as Motorola MC14001BCP. It also resets mode flipflop U9 pins 11 and 3 through the logic gate U10, pin 11. Integrated circuit U10 may suitably be a dual OR gate such as Motorola MC14071BCP. Pins 10 and 4 of the NOR gate U9 form the write/read flipflop control for the memory. Similarly, pins 11 and 3 of U9 form the timer control flipflop.

Pin 4 of the gate U9, which is normally logic zero, when reset, places the memory RAM devices U7 and U8 in the write mode. This allows the ADC, U4, to write data continuously into the memory at the rate of 100 samples per second at each succeeding address determined by the address counter U6. The logic zero also sets up a condition at the input pin 9 of OR gate U10 to select the continous or loop timer mode set up by the switch 26, which is schematically illustrated in FIG. 7 as a gang switch comprising switched connections S26-1, S26-2, S26-3 and S26-4.

The record mode is initiated by the patient pressing the store/record switch 12 on the exterior of the transmitter case 6. Pressing and releasing the switch 12 the first time sets the timer control flipflop U9, pins 11 and 3. Pressing the switch places a logic one at the input of logic inverter U5 pin 13. The output of the inverter, now logic zero, returns to logic one when the switch 12 is released by the patient user. This positive going change is differentiated by the network C22 and resistor R51. The resultant pulse sets the flipflop U9 pins 11 and 3 and resets the twelve bit binary counter U11, which may suitably be a Motorola MC14040BCP. A damping capacitor C24 and resistor R54 removes any transients from the signal out of switch 12.

The setting of NOR gate U9 does three things. First, a logic one is applied to input pin 2 of dual input NAND gate U12, which may suitably be a Motorola MC14011BCP. This logic one allows clock pulses from the main clock to pass through to the counter at pin 10 of U12. The counter U11 counts up clock pulses until the output decoder logic determines that the counter has reached the count to stop counting. This is accomplished by the setting of switch S26 to select the timing mode that was decided on by the monitoring physician. Switch 26 may be set to close any one of contacts S26-1, S26-2, S26-3, or S26-4. Closing of the contacts S26-1 selects an operation such that the transmitter counts for the full forty seconds subsequent to activation by the patient, and then stops. This does not allow any loop or continuous rewriting memory action, but records only the patient electrocardiogram (ECG) subsequent to pressing the record switch 12.

Closing of contacts S26-2, by selecting position 2 on switch 26, selects an operation such that counter U11 counts for thirty seconds after the activating button 12 is pressed. This allows for a loop memory operation of ten seconds before the patient action and thirty seconds after, by causing rewriting of the stored data over thirty seconds of the previously recorded forty second time increment. In a corresponding manner position 3 of switch 26, which represent the closing of switch S26-3 in FIG. 7, selects an operation such that the counter U11 counts for twenty seconds after the record switch 12 is pressed. This allows for a loop memory of twenty seconds before and twenty seconds after activation of switch 12. Finally, position 4 of switch 26, corresponding to closing of switch S26-4, selects an operation such that the counter counts for ten seconds after actuation of switch 12 so that the memory loop is thirty seconds before that actuation and ten seconds after.

From this description of the operation of the loop memory, it may be seen that the actuation of switch 12 serves to halt further storage of signals either 10, 20, 30 or 40 seconds after actuation. These delay periods are selected as predetermined portions of the total time increments, which in this embodiment is forty seconds. Thus, the predetermined event that halts further storage of signals in the RAM continuous storage may be seen to comprise the combination of actuation of switch 12 and the passage of the predetermined time increment portion subsequent to that actuation, which portion could be as small as zero.

The logic signal selected by the four positions of switch 26 passes through the selected switch and is differentiated by the network formed by capacitor C14 and resistor R30. The resulting negative going pulse is input into the OR gate U10 at pin 8. This pulse is "OR'ed" with the logic zero from pin 4 of NOR gate U9. The resulting negative going pulse passes from negative logic OR gate U12 pin 4.

The positive going pulse at this point passes to pin 9 of OR gate U9, changing the state of the record mode flipflop. This positive pulse is also "Or'ed" through the logic gate U10 pin 11. The positive pulse changes the state of the timer flipflop, stopping the count at this point. The changing state of the record flipflop changes the memory to the read mode and also stops any further clock pulses from passing through pin 11 of NAND gate U12.

The clock pulses, described above, are derived from the signal of the ADC indicating completion of the conversion. These pulses also update the address counter U6, so that when they stop, the address counter U6 remains at the last address in which it stored electrocardiographic data. Because this memory address counter actually counts forty seconds worth of addresses on each cycle, the very next address of this counter will be the very first address of forty seconds of electrocardiographic data. This first address will be the oldest data, corresponding to that at the beginning of that forty second time increment, and the last address will correspond to the point at which the counter has now stopped. Because the point in time at which the patient activates switch 12 of the unit cannot be predicted, the address locations that will be stored cannot be predicted. However, the fact remains that the address where the counter stopped will correspond to the last of the forty seconds of electrocardiographic data to be played back in the manner described below and will remain as that data until the memory is reset by briefly turning off the apparatus.

Because the subsequent readout of the data from the apparatus may be over a telephone line, the receiving location may have no direct knowledge of the setting of switch S26. This function is provided by the circuitry comprising U5, capacitor C25, resistor R55 and diode CR3. In this circuit a signal from pin 3 of U9 is provided to the buffer amplifier U6 at pin 10. Capacitor C25 and resistor R55 serve as a differentiating network looking for a positive going pulse from pin 10 of U6, resulting from the signal of U7 pin 3. When such a positive going pulse is received, it then passes through diode CR3 to pin 7 of the analog to digital converter U4. This pulse thus causes a momentary dc offset, which will then be stored in the RAM memory as a "false" signal that, when read out of the apparatus will provide a spike in the final analog signals, the position of which spike will thus indicate in which of the selected positions timing switch S26 has been set.

There is one remaining function to be described in the record mode. When pin 3 of NOR gate U9 goes to logic zero upon releasing by the patient of the record switch 12, this event pulls the cathode end of diode CR1 and also the junction of the anodes of diodes CR1 and CR2 and of resistor R31 to logic zero. These diodes CR1 and CR2, and also CR3 may suitably be type 1N914. The resultant signal through interconnect J1-7 between the digital board and the analog board enables the voltage controlled oscillator U13 on the analog board to turn on the audible output of the apparatus, which will be described below. The audible output is turned on as long as pin 3 of NOR gate U9 is at logic zero, which depends upon the setting of switch 26. While recording, the audible output will be modulated by the electrocardiographic patient data being recorded.

Once the apparatus has been activated by the using patient's actuation of switch 12 to store data, it will remain in the standby mode until the record switch 12 is again pressed. Usually, the patient will go to a telephone to transmit the stored data at a convenient time, depending upon the instructions from his individual physician. When the patient is ready to transmit and has contacted the receiving facility, he places the unit down on a surface, as illustrated in FIG. 5, places the telephone handset transmitter over the speaker hole 24 and into the recessed ring 22, shown in FIG. 3, and again presses the record button 12. The unit will then begin to transmit the entire forty seconds of stored data. The record button 12 changes the state of the timer flipflop as previously described. However, in the playback or output mode, the record flipflop will be in the read mode, allowing data to be read out of the memory. Read clock pulses from pin 3 of NAND gate U12 advances the timer counter U11 and pass through pin 3 of OR gate U10, through pin 11 of NAND gate U12, through inverter U5 pin 4 to the chip enable input of the memory devices U7 and U8 pin 18.

The clock pulses from pin 11 of NAND gate U12 also go to the address counter U6 as previously described. The timer count starts from time zero by virtue of being reset by the record switch 12 actuation, while the address counter begins at the last address held when the storing mode ended. The timer counter runs until the count is 4095 and then toggles over to zero. At this point the negative going edge is differentiated by the network of capacitor C15 and resistor R32. The resultant negative going pulse passes through pin 4 of OR gate U10 and through pin 4 of NAND gate U12, which again stops the timer mode, resetting the timer flipflop.

There remains one additional mode—the real time transmit mode. If the clinic or the patient's physician so requires, the using patient may transmit real time electrocardiographic data by pressing the record switch 12 and holding it depressed. When this is done the inverter U5 at pin 12 pulls the cathode of diode CR2 to logic zero. This turns on the voltage controlled oscillator U13, while the logic one at interconnect J1-6 turns on the C-MOS switch U3 on the analog board so that real time electrocardiographic data goes through pins 4 and 3 of of multiplexer U3 and through the low pass filter as described below.

The resultant current from the digital to analog converter (DAC) is applied to the input of a current to voltage converter amplifier U1 at pin 9. Resistor R33 serves to set the gain of this stage. At this point, the signal appears either as a stepping or pulsing signal (depending upon whether the apparatus is in a recording or output producing mode), resembling the original signal but 180 degrees out of phase. Pin 14 of U1 is configured as an inverting amplifier with a gain of one, set by resistors R59 and R60, to bring the signal back into phase with the original, for reasons to be described below.

In order to recover the two types of signals from the memory system, that is stepping and pulsing, an additional sample and hold circuit is used to hold the recovered signal in between samples. This is made up of pins 1 and 2 of C-MOS electronic switch U3 and capacitor C16. The control input pin 13 of U3 receives a signal from the digital board through interconnect J1-5. This signal can be any one of three. There is no signal if the unit has just stored a signal in memory and is in standby. There will be a pulse derived from the analog to digital converter (ADC) that indicates that the ADC has completed a conversion, or a pulse derived from the master clock that indicates that a readout is enabled from an address in memory and is available to be stored. This is one of the control signals of primary interest, because of the interest in the output that comes from the memory on playback. The recovered analog signal in this mode is pulsing and is transferred and held in the sample and hold capacitor C16 when the control signal indicates that the memory is ready.

Another input available to capacitor C16 is the real time signal from the patient input electrode. This signal can be transferred to capacitor C16 when the record switch 12 is pushed and held by the patient. When this occurs, a control signal is sent to the control input of pin 6 of U3. This control turns on pins 8 and 9 of U3, which gates through the clock signal on pin 12 of U3. Therefore, the control signal is applied to the control input of U3 pin 5, thus switching the analog signal on U3 pin 4 through to pin 3 and to capacitor C16. Thus, when the patient is instructed to transmit in real time to the receiving location, his pressing and holding the record switch 12 will transmit only the real time signal through the pins 3 and 4 connection of U3.

Because the signal on capacitor C16 is a stepping type of wave form, it is necessary to smooth the wave form so that it more nearly resembles the original signal. A low pass filter made up of resistors R34 and R35, capacitors C17 and C18, and output pin 7 of U2 is used as a smoothing filter. The filter is designed to have a cutoff frequency at 40 Hz and is of similar design to the above-described filter in the input circuit. However, it is designed to have a higher impedance level to avoid loading capacitor C16.

After smoothing, the signal is ready to be transmitted over telephone lines. This is accomplished by utilizing a voltage controlled oscillator (VCO) U13 to convert the analog waveform to a frequency modulated carrier in the 1600 Hz. range. Using one portion of integrated circuit U13, the analog waveform arrives through resistor R56 at pin 9 thereof, the VCO input. The oscillator, having a center frequency of approximately 1600 Hz, is modulated by internal current controlled amplifiers. The center frequency is set by external controls R36, R37, R38 and R39 and the capacitor C26. Input pin 5 of U13 is used to turn on the oscillator on command of the control logic. This input is driven to logic zero when the unit is requested by the patient either to record, to playback, or to transmit while pressing the record switch.

The output buffer amplifier U15 (which may be a TI type. TL064CN) receives at pin 1 the VCO output square wave that has been modulated by the analog waveform. The buffer amplifier output switches between the battery voltage level and a chassis ground level. This signal drives the speaker 34 through the current limiting resistor R40. The speaker may conveniently be derived from a piezoelectric diaphragm that responds to audio signals by "bending" in response to the driving voltage. This bending or deflection excites the air around it, causing a sound at the frequency of the driving signal. The speaker is mounted in the transmitter case so that it is suspended by the edges for maximum bending. The hole 24 in the case 8 is provided for the moving air and thus the sound to reach the telephone transmitter in the handset 32 mouthpiece.

This apparatus may conveniently operate on a single nine volt transistor radio battery. Power is brought into the unit through the power on/off switch 18. This switch 18 turns the unit on and off and also resets the logic, as described above, for the next recording. The current then passes to the interconnect terminal J2-1 from the digital circuitry (FIG. 7) to the analog circuitry (FIG. 6).

The battery voltage is applied to the integrated circuit U15, which is a quad operational amplifier. It is also applied to the collector of silicon transistor Q1, which may suitably be a Motorola MPS3704, and to resistor R41. Current from R41 passes through diode CR4, which preferably is a zener diode such as a TRW LVA51A, which has been chosen for its designed characteristic of regulating voltage over a large range of operating current. The 5.1 volts derived from this zener is applied to the voltage divider resistors R42 and R43, whose output is applied to pin 10 of U15. This divider sets up the final output voltage of 5.0 volts.

The output of pin 8 of U15 is applied to the base circuit of transistor Q1. U15 is wired as a follower, such that Q1 acts as a power booster at its emitter, which is included in the feedback loop at pin 9 of U15. Therefore, output voltage changes at the emitter of Q1 are compared to the reference voltage, and errors are amplified by U15 and applied to the base of Q1 to correct the changes. The 5.0 volt supply is preferably used as the power source for all of the remaining circuits in the transmitter except those associated with U15. Capacitor C19 acts as a filter capacitor to remove high frequency variations.

In order to operate the remaining signal amplifiers at a common mode point, sometimes referred to as a "fake ground", a 2.5 volt regulated supply is required. Five volt power is applied to the voltage divider, formed by resistors R44 and R45. This voltage, which is 2.5 volts, is then applied to pin 12 of U15. U15 here acts as a follower power booster whose output is fed back to the input pin 13. Therefore, any changes occurring at the output pin 14 are compared to the reference 2.5 volts. Capacitors C20 and C21 act as filter capacitors to remove any high frequency variations.

In order to detect imminent battery failure, a battery fail detector circuit is also provided. This circuit is made up of one portion of U15 at pin 7. The battery voltage is applied across the voltage divider R46 and R47. This divided voltage is compared to the reference voltage of 5.0 volt. As the battery voltage declines from use, the divided voltage at pin 6 of U15 will decrease until a point is reached when it is less than the reference level of 5.0 volts. At this point, the output of pin 7 of U15 will switch from a voltage near chassis ground to a voltage near the battery voltage. This will allow current to be supplied to the light emitting diode 20 through the resistor R48. R49 and R50 act as a positive feedback network to cause the output of pin 7 of U15 to "snap" to the battery voltage level. The cathode end of light emitting diode 20 is alternately switched to chassis ground through the clock output of pin 13 of U6 on the digital circuitry through the interconnect J1-4. Thus, the light emitting diode blinks when the battery voltage falls below the preset battery fail voltage.

An accompanying table of typical values indicates suitable values for the various resistors and capacitors utilized in this apparatus.

The foregoing describes one particularly preferred embodiment of the apparatus of this invention, along with its preferred method of operation. However, because numerous variations and modifications, all within the scope of the invention, will readily occur to those skilled in the art, this description is to be considered only as illustrative of the principles of the invention and is not to be limitative thereof. The scope of this invention is to be limited solely by the claims appended hereto.

What is claimed is:

1. Apparatus for monitoring and recording electrocardiographic data from a user, comprising
   a portable monitoring, storing and recording unit;
   sensing electrode means for sensing the user's electrocardiographic data, including data representative of a arrythmia episode;
   means for supporting said sensing electrode means on the user's body;
   amplifying means operatively connected to said electrode means for receiving therefrom and amplifying the analog electrical signals corresponding to said electrocardiographic data received from said electrode;
   means for converting the entire analog signals to digital signals corresponding to said electrocardiographic data;
   signal storage means for continuously receiving and storing said digital signals during successive predetermined time increments, said signal storage means including means for storing the digital signals representative to one time increment over the stored signals representative of a previous time increment, whereby the signals stored in the signal storage means at any given time comprise the signals received and stored during the most recent time increment;
   means operatively connected to said signal storage means for halting further said storage of said digital signals upon the occurrence of a predetermined event, whereby the signals stored in the signal storage means will include those signals corresponding to the electrocardiographic data for the most recent time increment immediately predeing the occurrence of said predetermined event; and
   means for providing an output of said stored signals for subsequent analysis of said electrocardiographic data.

2. The apparatus of claim 1 wherein said signal storage halting means comprises switch means actuatable by the user, such that said predetermined event comprises the actuation of said switch means.

3. The apparatus of claim 2 wherein said storage halting means further comprises timing means for delaying said storage halting by a predetermined portion of each time increment, such that said predetermined event is the combination of said switch actuation plus the passage of said predetermied time increment portion subsequent to actuation of said switch means.

4. The apparatus of claim 3 wherein said timing means for delaying said storage halting means includes means for selecting time increments of different lengths.

5. The apparatus of claim 4 wherein said means for selecting time increments of different lengths includes means for selecting time increments in the range of 10 seconds subsequent to said switch means actuation to 40 seconds subsequent to said switch means actuation.

6. The apparatus of claim 4 further comprising means for providing to said output a signal indicating which one of said time increments lengths has been selected.

7. The apparatus of claim 1 further comprising means operatively connected to said amplifying means for periodically sampling the analog signal received from said amplifying means and retaining the signal sample until a subsequent said periodic signal sample is received thereby and for providing said signal sample to said analog to digital converting means, whereby the analog signals converted by the analog to digital converting means comprise the sequential signal samples so retained.

8. The apparatus of claim 7 further comprising means operatively connected to said analog to digital signal converting means for controlling electrical energization of said continuous signal storage means such that said signal storage means is periodically energized to receive said converted signal sample and then deenergized until a subsequent said converted signal sample is received from said analog to digital converting means.

9. The apparatus of claim 1 wherein said output providing means comprises selectively actuatable means for retrieving said stored digital signals sequentially from said signal storage means, and means for converting said digital signals to analog signals corresponding to said electrocardiographic data.

10. The apparatus of claim 9 wherein said output providing means further comprises means for receiving from said digital converting means said analog signals converted from said sequential digital signals and combining said analog signals to form an output waveform.

11. The apparatus of claim 1 further comprising means for causing said analog signals from said amplifying means to bypass both said analog to digital converting means and said signal storage means and to go to said output providing means, whereby the amplified signals corresponding to the electrocardiographic data are made available for immediate analysis.

12. The apparatus of claim 1 wherein said amplifying means further comprises means selected operable to remove a predetermined bandwidth portion of said analog signal received from said electrode.

13. The apparatus of claim 12 wherein said bandwidth removing means comprises high pass filter means which passes only signals whose frequencies are above a predetermined lower cutoff frequency for processing as an output from the apparatus.

14. The apparatus of claim 12 further comprising means for selectively operating said filter means.

15. Portable apparatus for monitoring and storing data representative of the cardiac condition of a user, said apparatus comprising:
a portable monitoring unit;
means for dupporting the portable apparatus on the user's body;
means coupled with said portable unit for sensing the user's cardiac condition during a succession of predetermined time increments, including any arrhythmia event occurring during any time increment, and providing a data input to said portable unit representative thereof;
electronic circuit means carried by said portable unit including:
means for continuously receiving and storing entire signals representative of said data input from said electrode for each time increment, said receiving and storing means including means for storing said signals for each time increment over any earlier stored signals of a previous time increment,
means for initiating a halt to storage of signals by said storage means, and means for permitting operation of said storage means for a predetermined time period following initiation of said halt to storage; and wherein
means for providing an output of said stored signals the storage of data inputs for each time increment over data of a previous time increment permits continuous, remote operation of said portable apparatus until the occurrence of an arrhythmia in the user's cardiovascular system, at which time operation of said halt initiation means permits the retention of said data input for the most recent time increment.

16. The portable apparatus recited in claim 15 further comprising means selectively operable to remove a predetermine bandwidth portion of said data inputs received from said sensing means.

17. The portable apparatus recited in claim 16 wherein said bandwidth removing means comprises high pass filter means which passes only signals whose frequencies are above a predetermined lower cutoff frequency for processing as an output from said portable apparatus.

18. The partable apparatus recited in claim 15 wherein said halt initiation means comprises a switch operable by the user.

19. Portable apparatus for monitoring, storing and recording data representative of a cardiac condition of a user, said apparatus comprising:
a portable monitoring, storing and recording unit;
means for supporting the apparatus on the user's body;
means coupled with said portable unit for sensing the user's cardiac condition during a succession of predetermined time increments, including any arrhythmia event occurring during any time increment, and providing a data output to said portable unit representative thereof;
electronic circuit means carried by said portable unit, said circuit means having random access memory and indluding means defining
a continuous storage mode during which entire signals representative of the user's cardiac condition are continuously stored in said random access memory during said succession of predetermined time increments, said circuit means further including means for storing said signals for each time increment over any earlier stored signals of a previous time increment;
a record mode during which signals representative of the user's cardiac condition are in said random access memory during a predetermined time period;
said circuit means further including means for automatically stopping recording at the end of said predetermined time period; and
an output mode for reading said data representative of the cardiac condition of the user out of said random access memory,
means carried by said portable unit for switching between said storage, record, and output modes.

20. The portable apparatus recited in claim 19 wherein said electronic circuit means further comprises means for operating in said record mode for a delay period following switching to said record mode by said switching means.

21. The portable apparatus recited in claim 20 further comprising a multiple position switch carried by said portable unit for selectively varying the length of said delay period.

22. The portable apparatus recited in claim 19 wherein said electronic circuit means further comprises means for providing an audio output diring a portion of operation in said record mode, said audio output transmitting a signal representative of said user's cardiac condition.

23. The portable apparatus recited in claim 19 wherein said electronic circuit means further defines a real-time transmit mode for transmitting said data in real-time, said real-time transmit mode means responsive to continuous operation of said switch means.

24. A method for monitoring and recording data representative of the cardiac condition of a user, said method comprising the steps of:

provoding a portable monitoring and recording unit adapted to be carried by the user, said unit including an electrode for sensing the user's cardiac condition during successive predetermined time increments, including any arrythmia event occurring during any time increment, and providing a data output to said portable unit representative thereof;

continuously receiving and recording entire signals representative of said data input from said electrode for each time increment;

recording signals for each time increment over the earlier recorded signals of a previous time increment;

initiating a signal to halt further recording of daid signals responsive to an input from the user;

continuing the recording of said signals for a Predetermined time period following initiation of said halt signal and;

transmitting said signals to a central site for further analysis.

* * * * *